United States Patent
Schmutz

(10) Patent No.: US 7,465,723 B2
(45) Date of Patent: Dec. 16, 2008

(54) USE OF CARBOXAMIDES FOR THE TREATMENT OF TINNITUS

(75) Inventor: Markus Schmutz, Schoenenbuch (CH)

(73) Assignee: Novartis, East Hanover, NJ (US)

( * ) Notice: Subject to any disclaimer, the term of this patent is extended or adjusted under 35 U.S.C. 154(b) by 293 days.

(21) Appl. No.: 10/523,291

(22) PCT Filed: Aug. 5, 2003

(86) PCT No.: PCT/EP03/08669

§ 371 (c)(1), (2), (4) Date: Aug. 23, 2005

(87) PCT Pub. No.: WO2004/014391

PCT Pub. Date: Feb. 19, 2004

(65) Prior Publication Data

US 2006/0106009 A1    May 18, 2006

(30) Foreign Application Priority Data

Aug. 6, 2002 (GB) ................................. 0218243.4
Aug. 6, 2002 (GB) ................................. 0218244.2

(51) Int. Cl.
*A61P 27/16* (2006.01)
(52) U.S. Cl. ...................................................... 514/217
(58) Field of Classification Search ................... 514/217
See application file for complete search history.

(56) References Cited

FOREIGN PATENT DOCUMENTS

| EP | 0 646 374 | 4/1995 |
|---|---|---|
| EP | 0 751 129 | 1/1997 |
| WO | WO 00 01416 | 1/2000 |

OTHER PUBLICATIONS

Simpson, J. et al., Trends in Pharmacological Sciences, 20(1), Jan. 1999, pp. 12-18.*

* cited by examiner

*Primary Examiner*—Sreeni Padmanabhan
*Assistant Examiner*—Sahar Javanmard
(74) *Attorney, Agent, or Firm*—Kristin M. Nevins; Montgomery, McCracken, Walker & Rhoads, LLP

(57) ABSTRACT

The present invention relates to the use of carbamazepine derivatives in treating tinnitus.

5 Claims, No Drawings

USE OF CARBOXAMIDES FOR THE TREATMENT OF TINNITUS

The present invention relates to new pharmaceutical uses of carbamazepine derivatives.

More particularly the present invention relates to new pharmaceutical uses of the carbamazepine derivatives of formula I

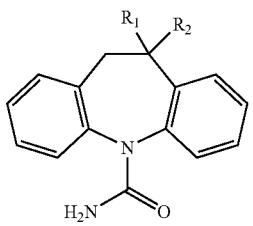

wherein
(a) $R_1$ represents hydrogen, and $R_2$ represents hydroxy or $C_1$-$C_3$alkyl carbonyloxy, or
(b) $R_1$ and $R_2$ together represent an oxo group, and of their pharmaceutically acceptable salts.

The preparation of the compound of formula I wherein $R_1$ is hydrogen and $R_2$ represents hydroxy and of its pharmaceutically acceptable salts is described, e.g., in U.S. Pat. No. 3,637,661. Such compound, monohydroxycarbamazepine, (10-hydroxy-10,11-dihydro-carbamazepine), the main metabolite of the antiepileptic oxcarbazepine (Trileptal®) is well known from the literature [see for example Schuetz H. et al., Xenobiotica (GB), 16(8), 769-778 (1986)]. The compound is indicated to be suitable for the treatment of psychosomatic disturbances, epilepsy, trigeminal neuralgia and cerebral spasticity.

The preparation of the compound of formula I wherein $R_1$ is hydrogen and $R_2$ represents $C_1$-$C_3$alkyl carbonyloxy and of the pharmaceutically acceptable salts thereof is described, e.g., in U.S. Pat. No. 5,753,646. The compounds are described to be efficacious against epilepsy.

The carbamazepine derivatives of formula I wherein $R_1$ represents hydrogen, and $R_2$ represents hydroxy or $C_1$-$C_3$alkyl carbonyloxy constitute chiral compounds. For the purposes of the present invention, the chiral compounds disclosed herein can be employed in the form of racemates, in mixtures comprising one enantiomer in excess (e.g., more S-10-hydroxy-10,11-dihydro-carbamazepine than R-10-hydroxy-10,11-dihydro-carbamazepine) or in enantiomerically pure form (e.g. pure S-10-hydroxy-10,11-dihydro-carbamazepine or pure S-10-acetoxy-10,11-dihydro-carbamazepine).

The compound of formula I wherein $R_1$ and $R_2$ together represent an oxo group is known as oxcarbazepine (10-oxo-10,11-dihydro-5H-dibenz[b,f]azepine-5-carboxamide, marketed e.g. under the brand name Trileptal®). Oxcarbazepine is a known anticonvulsant drug useful in the treatment of seizures of, for example, epileptic origin. Its preparation is described, e.g., in the German patent 2,011,087.

Tinnitus is the medical term for roaring, buzzing, clicking, whistling, hissing, or high pitched ringing in the ears or inside the head. Tinnitus may be constant or occur intermittently in one or both ears. Although there are many theories about how tinnitus occurs, there is no scientific consensus to its origin. Some causes of tinnitus result from a blow to the head, large doses of aspirin, anemia, noise exposure, stress, impacted wax, hypertension and certain types of medications and tumors.

The term "other inner ear/cochlear excitability related diseases" as used herein includes, but is not restricted to neuronal loss, hearing loss, sudden deafness, vertigo or Meniere's disease.

In accordance with the present invention, it has now surprisingly been found that the compounds of formula I in free base or acid addition salt form is useful in the prevention and treatment of tinnitus and other inner ear/cochlear excitability related diseases.

Hence, the present invention relates to the use of a compound of formula I wherein
(a) $R_1$ represents hydrogen, and $R_2$ represents hydroxy or $C_1$-$C_3$alkyl carbonyloxy, or
(b) $R_1$ and $R_2$ together represent an oxo group, or pharmaceutically acceptable salts thereof for the treatment of tinnitus or other inner ear/cochlear excitability related diseases.

In one preferred embodiment of the present invention, $R_1$ represents hydrogen and $R_2$ represent hydroxy.

In another preferred embodiment of the present invention, $R_1$ represents hydrogen and $R_2$ represents acetoxy.

In a further preferred embodiment of the present invention, $R_1$ and $R_2$ together represent an oxo group.

The activity in tinnitus of the compounds can be shown in standard tests, e.g. in the salicylate-induced tinnitus model in rats, or in tinnitus models in cats, and in particular in those models described herein.

It has been demonstrated [C. A. Bauer et al., Hearing Research 147 (2000) 175-182] that chronic salicylate exposure causes upregulation of glutamic acid decarboxylase (GAD) expression in the rat inferior colliculus (IC), associated with the development of tinnitus. Furthermore, electrophysiological recordings from auditory neurons using patch clamp recording techniques [D. Peruzzi et al. Neuroscience 101 (2000) 403-416, X. Lin et al., Journal of Neurophysiology 79 (1998) 2503-2512] and single neuron recordings [J. J. Eggermont and M. Kenmochi, Hearing Research 117 (1998) 149-160] showed that the excitability of neurons is changed following salicylate and quinine treatment.

Administration of salicylate or quinine caused an increase in the firing rate auditory neurons measured by extracellular electrophysiological recording techniques. Using in vitro electrophysiological recording techniques superfusion with salicylate increases the excitability of the recorded neurons. On administration of the compounds at concentrations of about 1 nM to 300 µM, the effects of salicylate were reversed.

The pharmacological activity of the compounds of formula I may, for example, also be evidenced in clinical studies known as such. Such clinical studies are preferably randomized, double-blind, clinical studies in patients with tinnitus. The beneficial effects on tinnitus can be determined, e.g., directly through the results of these studies.

For the treatment of tinnitus and the other conditions mentioned herein, appropriate dosage will of course vary depending upon, for example, the specific compound of formula I employed, the host, the mode of administration and the nature and severity of the condition being treated. However, in general, satisfactory results in animals are indicated to be obtained at a daily dosage of from about 1 to about 300 mg/kg animal body weight. In larger mammals, for example humans, an indicated daily dosage is in the range from about 10 to about 3000 mg of a compound of formula I, conveniently administered, for example, in divided doses up to four times a day.

The compounds of formula I may be administered in any usual manner, e.g. orally, for example in the form of tablets or capsules, or parenterally, for example in the form of injection solutions or suspensions.

The present invention also provides pharmaceutical compositions comprising a compound of formula I in association with at last one pharmaceutical carrier or diluent for use in the treatment of tinnitus. Such compositions may be manufactured in conventional manner.

Unit dosage forms may contain for example from about 2.5 mg to about 1000 mg of a compound of formula I.

The invention further provides the use of a compound of formula I for the manufacture of a pharmaceutical composition for the treatment of tinnitus and other inner ear/cochlear excitability related diseases such as neuronal loss, hearing loss, sudden deafness, vertigo or Meniere's disease.

The invention further provides a method for the treatment of tinnitus and other inner ear/cochlear excitability related diseases such as neuronal loss, hearing loss, sudden deafness, vertigo or Meniere's disease in a subject in need of such treatment, which comprises administering to said subject a therapeutically effective amount of a compound of formula I.

Racemates of compounds of formula I wherein $R_1$ represents hydrogen and $R_2$ represents hydroxy or $C_1$-$C_3$alkyl carbonyloxy can, e.g., be obtained by mixing the pure enantiomers of the respective compound of formula I. The pure enantiomers of a compound of formula I wherein $R_1$ represents hydrogen and $R_2$ represents hydroxy or $C_1$-$C_3$alkyl carbonyloxy can be obtained starting from the racemate by procedures known as such. The racemate may be separated into its enantiomers through the formation of diastereomeric salts, for example by salt formation with an enantiomer-pure chiral acid, or by means of chromatography, for example by HPLC, using chromatographic substrates with chiral ligands.

In one embodiment of the invention, the pure enantiomers of the compound of formula I wherein $R_1$ represents hydrogen and $R_2$ represents hydroxy are prepared according to the procedures described in the Examples.

The pure enantiomers of the compound of formula I wherein $R_1$ represents hydrogen and $R_2$ represents $C_1$-$C_3$alkyl carbonyloxy can be prepared, e.g., according to the procedures described in U.S. Pat. No. 5,753,646 or WO02/09257.

The term "enantiomerically pure form" as used herein means that a chiral compound is almost free of its enantiomer, i.e., a sample of the chiral compound comprises less than about 5, preferably less than about 2, more preferably less than about 0.5, weight percent of its enantiomer.

Hence, the present invention relates to the use of a compound of formula I, wherein $R_1$ represents hydrogen and $R_2$ represents hydroxy or $C_1$-$C_3$alkyl carbonyloxy, especially acetoxy, wherein the compound is employed in enantiomerically pure form, in particular of a compound of formula I having the S configuration.

The following Examples serve to illustrate the invention without limiting the invention in its scope.

| Abbreviations | |
|---|---|
| Ac | acetyl |
| aqu. | aqueous |
| dansyl | 5-(dimethylamino)-1-naphthalenesulfonyl |

| Abbreviations | |
|---|---|
| Et | ethyl |
| HPLC | high pressure liquid chromatography |
| Me | methyl |
| NMR | nuclear magnetic resonance |
| RT | room temperature |
| THF | tetrahydrofuran |
| Ts | tosyl |

EXAMPLES

Example 1

Procedure for the enantioselective Transfer Hydrogenation of 10-Oxo-10,11-dihydro-dibenzo[b,f]azepine-5-carboxylic acid amide to R(−)-10,11-Dihydro-10-hydroxy-5H-dibenz[b,f]azepine-5-carboxamide To a mixture of 10-oxo-10,11-dihydro-dibenzo[b,f]azepine-5-carboxylic acid amide (300 mg, 1.189 mmol) and RuCl[(1R,2R)-p-TsNCH($C_6H_5$)CH($C_6H_5$)$NH_2$]($\eta^6$-p-cymene, Aldrich, Switzerland) (8.8 mg, 0.0138 mmol) in $CH_2Cl_2$ (15 ml) is added dropwise a premixed solution of formic acid and NEt3 (5:2, 328 mg:289 mg) at 23° C. and stirred for 10 min. The clear solution is heated to reflux for 16 h. The reaction mixture is cooled to RT, diluted with $CH_2Cl_2$ (20 ml) and neutralised with aqu. $NaHCO_3$. After washing with brine the solution is concentrated under reduced pressure. The residue is purified by flash chromatography on silica gel using a 6:1 EtOAc-MeOH mixture as eluent to afford of R(−)-10,11-dihydro-10-hydroxy-5H-dibenzo[b,f]azepine-5-carboxamide (enantiomeric purity (ee)>99% determined by HPLC on Chiracel OD, Retention time: 9.46 min. $[\alpha]_D^{rt}=-195.3°$ (ethanol). $^1$H-NMR (400 MHz, $CDCl_3$): 7.70-7.20 (m, 8H), 5.30 (br s, 1H), 5.10-4.60 (br s, 2H), 3.75-3.40 (m, 1H), 3.20-2.90 (m, 1H), 2.50 (br s, 2H). NMR-Datas refer to Lit.: Benes, J et al., *J. Med. Chem.* 1999, 42, 2582-2587. Molecular weight: 254.291

Example 2

Procedure for the Enantioselective Transfer Hydrogenation of 10-Oxo-10,11-dihydro-dibenzo[b,f]azepine-5-carboxylic acid amide to S(+)-10,11-Dihydro-10-hydroxy-5H-dibenz[b,f]azepine-5-carboxamide To a mixture of 10-oxo-10,11-dihydro-dibenzo[b,f]azepine-5-carboxylic acid amide (300 mg, 1.189 mmol) and RuCl[(1S,2S)-p-TsNCH($C_6H_5$)CH($C_6H_5$)$NH_2$]($\eta^6$-p-cymene) (11 mg, 0.0173 mmol) in $CH_2Cl_2$ (15 ml) is added in two portions a premixed solution of formic acid and $NEt_3$ (5:2, 656 mg:578 mg) at 23° C. and stirred for 10 min. After that formic acid is added (50 µl) and the clear solution is heated to reflux for 16 h. The reaction mixture is cooled to RT, diluted with $CH_2Cl_2$ (20 ml) and neutralised with aqu. $NaHCO_3$. After washing with brine the solution is concentrated under reduced pressure. The residue is purified by flash chromatography on silica gel using a 6:1 EtOAc-MeOH mixture as eluent to afford of S(+)-10,11dihydro-10-hydroxy-5H-dibenzo[b,f]azepine-5carboxamide (ee>99% by HPLC on Chiracel OD). Retention time: 12.00 min. $[\alpha]_D^{rt}=+196.6°$ (ethanol). $^1$H-NMR (400 MHz, CDCl$_3$):7.70-7.20 (m, 8H), 5.30 (br s, 1H), 5.10-4.60 (br s, 2H), 3.75-3.40 (m, 1H), 3.20-2.90 (m, 1H), 2.50 (br s, 2H). NMR-Datas refer to Lit.: Benes, J et al., *J. Med. Chem.* 1999, 42, 2582-2587. Molecular weight: 254.291

Alternative production: To a mixture of 10-oxo-10,11-dihydro-dibenzo[b,f]azepine-5-carboxylic acid amide (300 mg, 1.189 mmol) and RuCl[(1 S,2S)-p-dansyl-NCH(C$_6$H$_5$)CH(C$_6$H$_5$)NH$_2$]($\eta^6$-p-cymene) (8.5 mg, 0.012 mmol) in CH$_2$Cl$_2$ (15 ml) is added dropwise a premixed solution of formic acid and NEt3 (5:2, 328 mg:289 mg) at 23° C. and stirred for 10 min. The clear solution is heated to reflux for 16 h. The reaction mixture is cooled to RT, diluted with CH$_2$Cl$_2$ (20 ml) and neutralised with aqu. NaHCO$_3$. After washing with brine the solution is concentrated under reduced pressure. The residue is purified by flash chromatography on silica gel using a 6:1 EtOAc-MeOH mixture as eluent to afford of S(+)-10,11-dihydro-10-hydroxy-5H-dibenzo[b,f]azepine-5-carboxamide.

Example 3

Preparation of RuCl[(1S,2S)-p-dansylNCH(C$_6$H$_5$)CH(C$_6$H$_5$)NH$_2$]($\eta^6$-p-cymene)

a) Preparation of (S,S)-5-dimethylamino-naphthalene-1-sulfonic acid (2-amino-1,2-diphenyl-ethyl)-amide: To a solution of (S,S)-diphenylethylenediamine (250 mg, 1.2 mmol) and triethylamine (0.5 ml) in THF is added dropwise a solution of dansyl chloride (318 mg, 1.2 mmol) in THF (2 ml) at 0° C. After stirring 16 h at RT the solvent is removed in vacuum and the residue is resolved in methylenchloride (20 ml). The organic solution is washed with NaHCO$_3$ solution (5 ml), dried over Na$_2$SO$_4$ and after filtration the solvent is removed. Flash chromatographie afford (S,S)-5-dimethylamino-naphthalene-1-sulfonic acid (2-amino-1,2-diphenyl-ethyl)-amide as yellow oil which crystallizes by drying in vacuum. M: 445.59. $^1$H-NMR (400 MHz, CDCl$_3$):8.36 (t, J=7.5 Hz, 2H), 8.17 (dd, J=7.2, 1.2 Hz, 1H), 7.47 (dd, J=8.8 Hz, 1H), 7.34 (dd, J=8.5 Hz, 1H), 7.24-7.16 (m, 4H), 7.11 (d, J=7.5 Hz, 1H), 6.99-6.74 (m, 6H), 4.61 (d, J=8.5 Hz, 1H), 4.20 (d, J=8.5 Hz, 1H), 2.80 (s, 6H).

b) Preparation of RuCl[(1S,2S)-p-dansylNCH(C$_6$H$_5$)CH(C$_6$H$_5$)NH$_2$]($\eta^6$-p-cymene): A solution of (S,S)-5-dimethylamino-naphthalene-1-sulfonic acid (2-amino-1,2-diphenyl-ethyl)-amide (80 mg, 0.18 mmol), NEt$_3$ (36 mg, 0.36 mmol) and [RuCl$_2$(p-cymene)]$_2$ (55 mg, 0.09 mmol) in 2-propanol is heated at 80° C for 1 h. The solvent is removed after that und the dark red residue is washed with water (2 ml). The solid is dried in vacuum and used without any purification. M: 715.34.

The invention claimed is:

1. A method of treatment for tinnitus in a subject in need of such treatment, which comprises administering to said subject a therapeutically effective amount of a compound of formula I

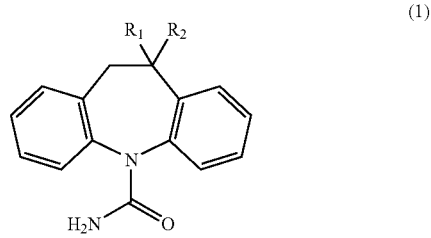

wherein
(a) R$_1$ represents hydrogen, and R$_2$ represents hydroxy or C$_1$-C$_3$ alkyl carbonyloxy, or
(b) R$_1$ and R$_2$ together represent an oxo group, or pharmaceutically acceptable salt thereof.

2. A method of treatment according to claim 1 wherein R$_1$ and R$_2$ of formula I or pharmaceutically acceptable salt thereof together represent an oxo group.

3. A method of treatment according to claim 1 wherein R$_1$ of formula I or pharmaceutically acceptable salt thereof represent hydrogen and R$_2$ represents hydroxy.

4. A method of treatment according to claim 1 wherein R$_1$ of formula I or pharmaceutically acceptable salt thereof represent hydrogen and R$_2$ represents acetoxy.

5. A method of treatment according to claim 1 wherein R$_1$ of formula I represents hydrogen and R$_2$ represents hydroxy or C$_1$-C$_3$ alkyl carbonyloxy and wherein the compound is employed in enantiomerically pure form.

* * * * *

UNITED STATES PATENT AND TRADEMARK OFFICE
CERTIFICATE OF CORRECTION

| | |
|---|---|
| PATENT NO. | : 7,465,723 B2 |
| APPLICATION NO. | : 10/523291 |
| DATED | : December 16, 2008 |
| INVENTOR(S) | : Markus Schmutz |

It is certified that error appears in the above-identified patent and that said Letters Patent is hereby corrected as shown below:

On the cover page at (73), please correct the Assignee's Name as follows:

Novartis AG, Basel (CH)

Signed and Sealed this

Seventh Day of July, 2009

JOHN DOLL
*Acting Director of the United States Patent and Trademark Office*